United States Patent [19]
Greene et al.

[11] Patent Number: 6,008,415
[45] Date of Patent: Dec. 28, 1999

[54] CYCLOHEXANE OXIDATION

[75] Inventors: Marvin I. Greene, Wyckoff; Charles Summer, Livingston; Robert J. Gartside, Summit, all of N.J.

[73] Assignee: ABB Lummus Global Inc., Bloomfield, N.J.

[21] Appl. No.: 09/119,074

[22] Filed: Jul. 10, 1998

Related U.S. Application Data

[63] Continuation of application No. 08/712,478, Sep. 11, 1996, Pat. No. 5,780,683.

[51] Int. Cl.$^6$ .................................................. C07C 45/33
[52] U.S. Cl. ........................... 568/358; 568/342; 568/350; 568/836
[58] Field of Search ................................... 568/358, 342, 568/350, 836

[56] References Cited

U.S. PATENT DOCUMENTS

| | | | |
|---|---|---|---|
| 3,530,185 | 9/1970 | Pugi | 568/342 |
| 3,694,511 | 9/1972 | Nouvel | 568/342 |
| 3,927,108 | 12/1975 | van de Moesgijk et al. | 568/342 |
| 4,238,415 | 12/1980 | Bryan | 568/342 |
| 4,328,175 | 5/1982 | Roeckel et al. | 261/91 |
| 4,341,907 | 7/1982 | Zelonka | 568/360 |
| 4,454,077 | 6/1984 | Litz | 261/91 |
| 4,720,592 | 1/1988 | Besman et al. | 568/342 |
| 4,900,480 | 2/1990 | Litz et al. | 261/36.1 |
| 5,041,682 | 8/1991 | Hartig et al. | 568/342 |
| 5,200,075 | 4/1993 | Ember | 568/573 |
| 5,371,283 | 12/1994 | Kingsley et al. | 562/416 |
| 5,523,474 | 6/1996 | Kingsley | 562/416 |

*Primary Examiner*—James H. Reamer
*Attorney, Agent, or Firm*—Alix, Yale & Ristas, LLP

[57] ABSTRACT

Cyclohexane is catalytically oxidized to produce cyclohexanol and cyclohexanone and precursors of these products. The oxidation is carried out in a liquid oxidation reactor at high oxygen concentrations (greater than 30% and preferably greater than 90% oxygen concentration) and at relatively low temperatures (less than 160° C.). The use of the liquid oxidation reactor permits the use of these high oxygen concentrations without forming dangerously high levels of oxygen in the overhead gas phase. The result is an increased yield and selectivity of the desired products.

9 Claims, 2 Drawing Sheets

CYCLOHEXANE OXIDATION

This is a continuation of application Ser. No. 08/712,478, filed Sep. 11, 1996 now U.S. Pat. No. 5,780,683.

BACKGROUND OF THE INVENTION

The present invention relates to the oxidation of cyclohexane for the production of cyclohexanol and cyclohexanone and most particularly to the use of liquid oxidation reactors using pure oxygen or oxygen enriched air and operating at temperatures which are somewhat lower or with reaction contact times which are shorter than conventionally used in cyclohexane oxidizers.

Most of the worldwide production of caprolactam and adipic acid, which are used in the manufacture of synthetics such as nylon, is based on the air oxidation of cyclohexane. The air oxidation of cyclohexane produces cyclohexanol and cyclohexanone and a variety of potential cyclohexanol and cyclohexanone precursors such as hydroperoxides which are then thermally and/or catalytically decomposed to produce additional cyclohexanol and cyclohexanone. The cyclohexanol and cyclohexanone are then used to produce either the caprolactam or adipic acid. The prior art processes for oxidizing cyclohexane employ air and operate at temperatures in the range of 130 to 180° C. in bubble columns or autoclaves. At the lower temperatures, 130 to 160° C., the reaction rates tend to be lower although the selectivity for the desired precursors is higher. At higher temperatures, the reaction rates increase but the selectivity is lower and more lower valued byproducts are produced.

The reaction rate and selectivity would be increased by raising the partial pressure of the $O_2$ above 21% but that cannot be done using conventional oxidizing systems because of safety problems. If the oxygen concentration is increased, to any significant degree, the oxygen level in the gas phase above the liquid increases and can readily reach a flammability limit which is usually above about 1% oxygen.

SUMMARY OF THE INVENTION

A process for the production of cyclohexanol and cyclohexanone by the oxidation of cyclohexane uses an oxidation process which is at relatively low temperatures in the range of 80° C. to 160° C. and at high oxygen concentrations, at least 30% and preferably greater than 90% and including essentially pure oxygen. The oxidation process is carried out in such a way that the oxygen concentration in the gas phase over the liquid is at safe levels. More specifically, the oxidation process is carried out in a liquid oxidation reactor which limits the escape of oxygen from the bubbly liquid phase to the gas space at the top of the reactor and, together with the injection of an inert gas stream into the gas space, thereby maintains the oxygen concentration in the gas space below the flammable or explosive limit. The result is an increase in the yield and selectivity of cyclohexanol and cyclohexanone and their precursors per unit of cyclohexane fed all at a lower temperature range. Following the liquid phase oxidation step using the liquid oxidation reactor, the reactor effluent may be subjected to a conventional thermal/catalytic decomposition of the precursors to produce product. Alternately, the effluent could be passed through a hydrogenation step where the yields are increased even further.

DESCRIPTION OF THE PREFERRED EMBODIMENT

In the present invention, cyclohexane is oxidized under the conditions which will be described in order to increase the yield of the desired oxidation products which include cyclohexanol and cyclohexanone and a series of cyclohexanol and cyclohexanone precursors as well as some undesirable oxidation products. The precursors are then catalytically hydrogenated to produce additional cyclohexanol and cyclohexanone. These precursors are believed to include, but not be limited to, one or more of cyclohexyl hydroperoxide, ketals, acetals, 1,1' oxybiscyclohexane, cyclohexyl esters of monocarboxylic and dicarboxylic acids, 7-oxabicyclo[4.1.0] heptane, 2-hydroxycyclohexanone, 2h-pyran-2-one tetrahydro, 2-oxepanone. Of these precursors, cyclohexyl hydroperoxide is one of the most abundant. In the prior art conventional cyclohexane oxidation processes, a significant percentage of the precursor cyclohexyl hydroperoxide can be converted either thermally or catalytically to cyclohexanol and cyclohexanone. However, the other precursors are not converted and represent a loss of selectivity. The hydrogenation step used in the present invention does transform these other precursors, which are not readily amenable to thermal or catalytic conversion, to cyclohexanol and cyclohexanone. As indicated, the oxidation process is carried out at temperatures below 160° C., preferably in the range of 80 to 145° C., and at oxygen concentrations of at least 30%, preferably in excess of 90% and including essentially pure oxygen which is in excess of 99% oxygen. Therefore, the oxidation may be carried out with pure oxygen or with oxygen enriched air. Conventional cyclohexane oxidation catalysts are employed such as soluble transition metal compounds. For example, the oxidation catalyst may be a cobalt ester of naphthenic acid, octanoic acid, 2-ethylhexanoic acid or other carboxylic acids. These catalysts serve to regulate free radical concentrations and are especially important for the conventional thermal decomposition of cyclohexyl hydroperoxide. Although the use of an oxidation catalyst in the liquid oxidation reactor is preferred, the catalyst may be omitted. The oxidation without a catalyst maximizes the formation of the hydroperoxide which can be readily converted to cyclohexanol and cyclohexanone in the hydrogenation step of the present invention.

Figure 1:
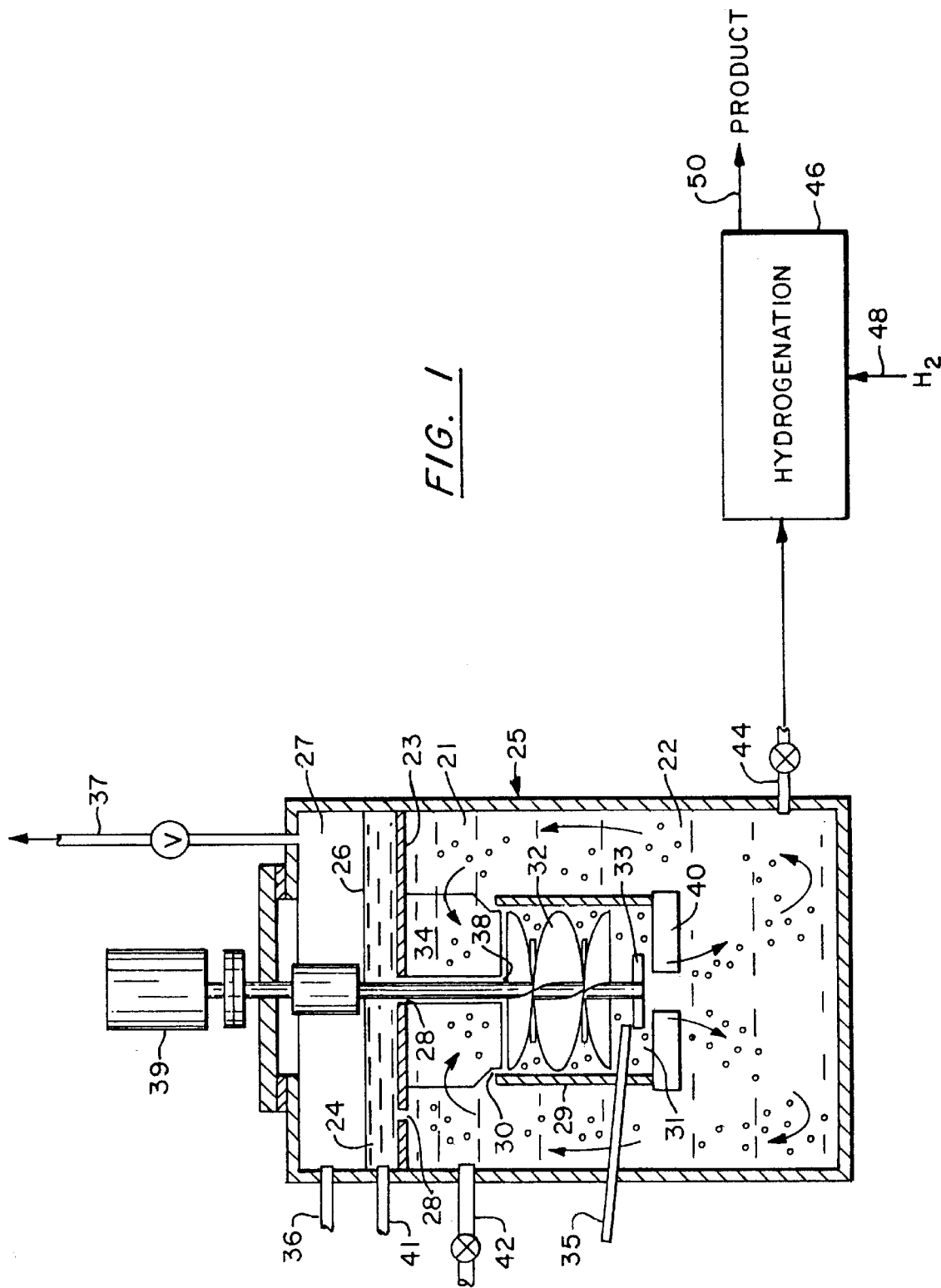
FIG. 1 is a flow diagram of the present invention which also depicts one version of a liquid oxidation reactor.
Figure 2:
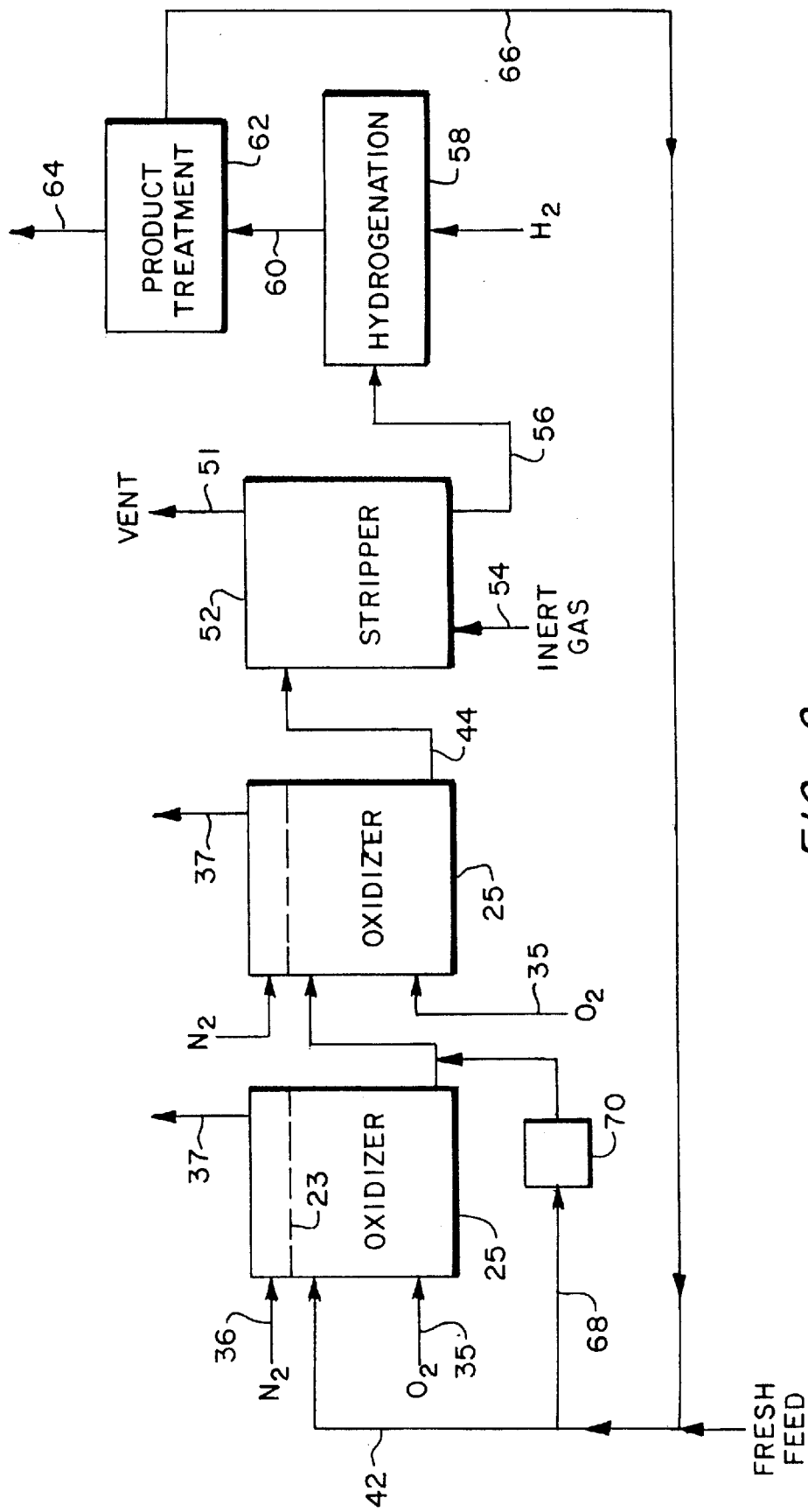
FIG. 2 is a flow diagram illustrating an alternate embodiment of the invention.

The oxidation is carried out in what is referred to as a liquid oxidation reactor. This is a reactor which has a main or major portion of liquid into which the oxygen is bubbled and which is maintained in a recirculating flow condition, a minor quiescent liquid portion, and a minor gas phase located above the quiescent liquid layer. The main body of liquid is separated by mechanical means from the relatively quiescent portion of the liquid. There is fluid communication between the two bodies of liquid and the quiescent portion has a gas-liquid interface with an overhead gas phase. The bubbles of gas formed in the liquid are maintained essentially in dispersed form in the recirculating liquid in the major portion of the body of liquid and no appreciable loss of gas occurs to the overhead gas phase. The drawing generally illustrates the oxidation and hydrogenation steps of the invention and illustrates the general construction of such a liquid oxidation reactor. Although FIG. 1 of the drawings only illustrates one liquid oxidation reactor, there would normally be a number of them in series as shown in FIG. 2, and perhaps as many as three or four.

Liquid oxidation reactors are disclosed and described in U.S. Pat. Nos. 4,900,480 and 5,371,283 as well as in the drawing hereof. Referring to FIG. 1, the reactor vessel 25 contains the major portion 22 of liquid body 21 which is separated by baffle means 23 from the quiescent portion of liquid 24. The quiescent portion 24 has a gas-liquid interface 26 with overhead gas phase 27. The baffle means 23 has a number of openings 28 located across the surface. These openings 28 establish fluid communication between major liquid portion 22 and quiescent liquid portion 24. There are many variations possible for the arrangement of the pattern of openings 28. The preferred pattern would direct most of the residual gas from the major portion 24 to a point close to the point of entrance of the inert gas 36 such that oxygen concentrations are always maintained below the flammable limits in the gas phase. The major portion of liquid 22 is maintained in recirculating flow conditions by the essentially central positioning within reactor vessel 25 of a hollow draft chamber 29 such that the open ends thereof, i.e., ends 30 and 31, are at the top and bottom thereof, respectively, and impeller means 32 is positioned within the hollow draft chamber 29. Such impeller means 32 are typically helical impeller means adapted to facilitate the downward flow of the oxygen bubble-liquid mixture in the draft chamber and upward flow outside the chamber. Impeller means 32 may, if desired, include radial flow impeller means 33 and lower baffle means 40, similar to the guide baffle means referred to below, to reduce the size of the oxygen bubbles that are maintained in the indicated recirculating flow conditions as the oxygen bubble-liquid mixture in major portion 22 of liquid body 21 is caused to pass downward through hollow draft chamber 29 and up to the outer sides of hollow draft chamber 29. The flow of the oxygen bubble-liquid mixture into the top end 30 and out of the bottom end 31 of the hollow draft chamber 29 is desirably facilitated by directing the mixture to the top inlet end 30 by guide baffle means 34 positioned at the upper portion of the major portion 22 of liquid body 21 below baffle means 23.

The feed oxygen stream is injected directly into the major portion 22 of the liquid body 21 through conduit means 35 so that the bubbles of oxygen formed in the liquid are readily maintained, essentially in dispersed form, in the recirculating liquid in the major portion of the body of liquid. One or more gas inlet means 36 and outlet vent means 37 are provided to enable nitrogen or other inert gas to be passed, if desired, through the overhead gas phase 27 to assure that the concentration of oxygen is maintained below the flammability limit. An additional inert gas stream 41, such as nitrogen, may be injected directly into the quiescent liquid layer 24 for sub-cooling, thereby reducing the need for evaporative cooling to remove the heat of reaction. Impeller means 32 include a suitable drive shaft 38 that extends upward through an opening 28 in baffle means 23 for connection with suitable driving means generally represented by the numeral 39.

The liquid oxidation system, as described above and variations thereof, enables pure oxygen or oxygen enriched air to be safely employed in place of normal air for the oxidation of cyclohexane. The conventional air sparger system as used in the prior normal air oxidizers are not suitable and would generally be inefficient if used with oxygen instead of air. In the oxygen based process of the invention, the amount of nitrogen that is introduced into the process, and therefore, the amount of vent gas that must be treated, is reduced by a factor of as much as 24 compared to the nitrogen introduced with the air in the conventional air based process. This is based on 99% oxygen utilization in the case of a liquid oxidation reactor and 5% oxygen in the vent gases in the case of conventional oxidation using air. Thus, the capital and operating expenses associated with air compression and vent gas treating are greatly reduced compared to the air base process.

In the operation of the oxygen based process of the invention in the liquid oxidation reactor system, oxygen is preferably fed near the bottom of the draft chamber 29 as shown in FIG. 1. Alternate locations for oxygen introduction are possible including but not limited to below the draft tube outlet, directly into the draft tube, or through orificed distribution systems located either above or below the draft tube. The exact location of the oxygen injection can be selected to influence the dispersion of bubbles and hence the efficiency of reaction. The horizontal baffle 23 allows some gas leakage to prevent the build-up of waste gases in the reaction zone. A purge stream of nitrogen or other inert gas is blown across the liquid surface of the quiescent zone to reduce the oxygen concentration in the headspace. The flow rate of the purge stream is adjusted such that the concentration of oxygen in the headspace is maintained below the explosive limit. For the illustrated system and generally in the practice of the invention, the oxygen concentration in the vent is suitably maintained below 5%, typically below 2%. The pressure in the liquid oxidation reactor is usually maintained in the range of 7 to 20 bars and preferably 8 to 10 bars.

In the present invention, the feed of cyclohexane is introduced into the reactor at 42 and the oxidized cyclohexane is withdrawn at 44. Although the reaction may be carried out on a batch basis, the preferred operation is continuous. In one configuration of the invention, the oxidized cyclohexane 44 which now contains cyclohexanol and cyclohexanone and one or more of their precursors previously mentioned, such as the hydroperoxides, is fed to the hydrogenerator 46 along with hydrogen stream 48. The known hydrogenation process thereby converts these precursors into additional cyclohexanol and cyclohexanone which are withdrawn as product 50. Typical thermal/catalytic decomposition of the cyclohexyl hydroperoxide occurs at approximately 75% efficiency. By employing the hydrogenation step on the effluent from a liquid oxidation reactor, these precursors can be converted to valuable products at very high selectivity approaching 100%. The combination of a liquid oxidation reactor which increases precursor yield with a very efficient precursor conversion step results in extremely high overall product yield. The hydrogenation catalyst may take the form of a heterogenous fixed bed catalyst, a slurry phase catalyst or a homogeneous catalyst. The catalyst may be any one of the conventional hydrogenation catalysts such as the noble metals. The noble metal is normally supported on an inert carrier such as palladium on a high surface area carbon support.

The performance of a cyclohexane oxidation reactor, i.e., the rate of production of the cyclohexanol, cyclohexanone and their precursor products and the selectivity to these products, is a function of reaction severity. In turn, the severity is a function of liquid residence time, temperature, oxygen concentration in the oxidant feed gas, catalyst concentration, and certain hydrodynamics-related parameters. The higher concentration of oxygen in the oxidant feed gas plus the improved hydrodynamics of the liquid oxidation reactor arrangement allows operation at either lower temperature or shorter residence time or a combination of both. In the present invention, when all other parameters are held constant, these combinations of residence time and temperature result in performance improvements by reducing the extent of undesired reactions.

Directionally, shorter residence times and lower temperatures than conventionally used (160° C. and 36 to 45 minutes liquids residence time with air) favor the improved performance when using the liquid oxidation reactor mixing system with high purity oxygen. For example, at a temperature of 130° C., the residence time might be about 40 minutes whereas it might be 8 minutes at 150° C. Those versed in the art of cyclohexane oxidation will appreciate that there are a multitude of other combinations possible. In addition to the improved selectivity, the reduction in residence time increases the productivity of a given reactor by reducing the ratio of liquid volume to volumetric feed rate. This provides a savings in reactor size and cost.

In order to illustrate the effects of the present invention as compared to cyclohexane oxidation at higher temperatures and with normal air, the following table lists the product selectivity:

|  | Conventional Technology | | Invention Claimed | |
| --- | --- | --- | --- | --- |
|  | Oxidation Reactor | Decomposition Reactor | Oxidation Reactor | Hydrogenation Reactor |
| % Oxygen in Oxidant | 21 | N.A. | 100 | N.A. |
| Temperature, C. | 160 | 160 | 149 | 149 |
| Pressure, Bar | 9 | 9 | 9 | 9 |
| Liquid Residence Time, min | 36 | 36 | 8 | 45 |
| Catalyst Concentration, ppm | 0.8 | N.A. | 0.6 | N.A. |
| Hydrogenation LHSV, hr.$^{-1}$ | N.A. | N.A. | N.A. | 80 |
| % Cyclohexane Conversion | 4 | 4 | 4 | 4 |
| % Selectivity: |  |  |  |  |
| Cyclohexanone | 20 | 24 | 34 | 40 |
| Cyclohexanol | 42 | 50 | 44 | 50 |
| PRECURSORS | 16 | 0 | 6 | 0 |
| TOTAL USABLE PRODUCTS | 78 | 74 | 84 | 90 |
| Productivity, gmol/hr.L | 0.45 | N.A. | 1.85 | N.A. |

It can be seen that even when conventional oxidation products are subjected to thermal catalytic decomposition, there is actually a reduction in the amount of the usable products. The invention increases the ultimate yield of cyclohexanol and cyclohexanone from a level of about 74 mole % to a level of about 90 mole %.

In the invention, the oxidation step is very quickly followed by the hydrogenation step. A continuum of the reaction temperature and total operating pressure is maintained between the two stages. This immediate hydrogenation is critical since the precursors of cyclohexanol and cyclohexanone would rapidly decompose to unusable byproducts if the oxidation product were allowed to sit at the reaction temperature. As an alternative, the effluent liquid from the oxidation reactor may be stripped using an inert gas in a stripper with a short liquid residence time prior to being sent to the liquid phase hydrogenation step. This stripping step removes residual oxygen from the effluent mixture of cyclohexane and oxygenated products. By rapidly removing dissolved oxygen, further decomposition reactions are minimized. In addition, any dissolved carbon monoxide, a known hydrogenation catalyst poison, is removed, thereby improving catalyst life. This embodiment is illustrated in FIG. 2 in which the oxidized product 44 from the liquid oxidation reactor 25 is fed to stripper 52. The inert gas 54, such as nitrogen, strips oxygen and CO from the liquid and discharges through vent 51. The liquid product containing the cyclohexanone and cyclohexanol is sent to the hydrogenation reactor 58 via line 56. The stripper also serves an important safety function by isolating the oxidation section from the hydrogenation. FIG. 2 also illustrates a plurality of reactors 25 in series.

This FIG. 2 further illustrates the separation of the product from the remaining unreacted cyclohexane and an arrangement for removing or controlling the heat of reaction. The effluent 60 from the hydrogenation step 58 is processed at 62, such as by distillation, resulting in the separation of the product cyclohexanol and cyclohexanone stream 64 leaving the stream 66 containing the unreacted cyclohexane. This stream 66 is then combined with the fresh cyclohexane feed to form the feed stream 42. As shown, the cyclohexane feed 42 is fed into the first of the liquid oxidation reactors 25. This feed, the majority of which is actually the recycled, unreacted cyclohexane 66 plus some fresh make-up cyclohexane, is maintained at the desired reaction temperature. A side stream 68 of this feed is cooled at 70 and fed into the second of the reactors 25 and would preferably be fed into each of the downstream reactors in a multi-reactor series. This cooled feed side stream quenches the feed to these reactors, thereby removing the heat of reaction and controlling the temperature while reducing evaporative cooling.

Another aspect of the present invention is that it can be incorporated into existing cyclohexane oxidation plants as a retrofit. In such an arrangement, at least some of the existing oxidizer capacity of the plant, such as a bubble column, can be employed to carry out an initial, partial oxidation which is then followed by the oxidation process of the present invention. In this way, the benefits of the present invention are realized but using smaller liquid oxidation reactors. In the bubble column or autoclave, the reaction temperature and/or the feed rate of air is reduced. This lowers the level of conversion of cyclohexane in the bubble column or autoclave from perhaps about 5% down to about 1%. The effluent from this first reactor is then sent to the one or more liquid oxidation reactors for completion of the oxidation process.

In the present invention, by operating in an oxygen-rich atmosphere in the liquid oxidation reactor, the severity of the oxidation reaction is modified in the direction which favors the enhancement of the production of cyclohexanone and cyclohexanol and their precursors, with cyclohexyl hydroperoxide being one of the most prevalent ones. In the conventional process, the cyclohexyl hydroperoxide and other precursors are thermally decomposed at oxidizer reaction temperature which results in only about 75% selectivity to the desired cyclohexanol and cyclohexanone products. Alternative technologies utilize catalytic agents at reduced temperatures to convert the precursors at higher selectivities, but these systems result in additional equipment costs and poorer thermal efficiencies associated with cooling and reheating the recycle streams. By coupling hydrogenation to the oxidizer effluent stream and maintaining process temperature in the present invention, it is possible to maximize the conversion of these precursors to the desired cyclohexanol and cyclohexanone products. Based on the widely used analytical technique of Iodine Number for measuring cyclohexyl hydroperoxide content of oxidate streams, it has been found that the incremental selectivity to cyclohexanone and cyclohexanol production during hydrogenation of the oxidates from the liquid oxidation reactor can exceed 100%. This unexpected increase is attributed to the selective conversion of the other precursors to cyclohexanol and cyclohexanone.

We claim:

1. A method for the production of cyclohexanol and cyclohexanone by the oxidation of cyclohexane in a liquid phase comprising the step of bubbling an oxygen-enriched gas stream containing at least 30% oxygen through said liquid phase and maintaining a temperature in said liquid phase below 160° C.

2. A method as recited in claim 1 wherein said liquid phase is maintained at a temperature in the range of 80 to 145° C.

3. A method as recited in claim 1 wherein said gas stream contains at least 90% oxygen.

4. A method as recited in claim 3 wherein said gas stream contains at least 99% oxygen.

5. A method as recited in claim 3 wherein an overhead gas phase is maintained above said liquid phase and including the step of restricting the passage of said gas stream from said liquid phase into said overhead gas phase.

6. A method as recited in claim 5 wherein the concentration of oxygen in said overhead gas phase is maintained at 5% or less.

7. A method as recited in claim 1 wherein the percent selectivity for cyclohexanone and cyclohexanol is increased as compared to a process using oxidation with air.

8. A method as recited in claim 7 wherein said increase in percent selectivity is 16%.

9. A method as regited in claim 1 wherein the percent selectivity for cyclohexanone, cyclohexanol and precursors is increased 6% as compared to a process using air oxidation.

* * * * *